(12) United States Patent
Taizou (10) Patent No.: US 11,602,587 B2
(45) Date of Patent: Mar. 14, 2023

(54) DEVICE FOR TREATING FAT CELLS TAKEN FROM A PATIENT AND INTENDED FOR A TRANSPLANT

(71) Applicant: Establishment Labs S.A., Alajuela (CR)

(72) Inventor: Najib Taizou, Sainte-Gemme-Martaillac (FR)

(73) Assignee: Establishment Labs S A, Alajuela (CR)

( * ) Notice: Subject to any disclaimer, the term of this patent is extended or adjusted under 35 U.S.C. 154(b) by 650 days.

(21) Appl. No.: 16/604,307

(22) PCT Filed: Apr. 6, 2018

(86) PCT No.: PCT/FR2018/000076
§ 371 (c)(1),
(2) Date: Oct. 10, 2019

(87) PCT Pub. No.: WO2018/189431
PCT Pub. Date: Oct. 18, 2018

(65) Prior Publication Data
US 2020/0061259 A1    Feb. 27, 2020

(30) Foreign Application Priority Data

Apr. 11, 2017   (FR) .................................. FR1770365

(51) Int. Cl.
*A61M 1/00*    (2006.01)

(52) U.S. Cl.
CPC .............. *A61M 1/88* (2021.05); *A61M 1/892* (2021.05); *A61M 1/895* (2021.05); *A61M 1/65* (2021.05);

(Continued)

(58) Field of Classification Search
CPC ....... A61B 2017/00792; A61L 27/3616; A61L 27/3683; A61L 2430/34; A61L 2430/40;
(Continued)

(56) References Cited

U.S. PATENT DOCUMENTS 5,372,945 A * 12/1994 Alchas ................... C12M 45/09
                                                    435/308.1
5,786,207 A *  7/1998 Katz ...................... C12M 45/05
                                                    435/308.1

(Continued)

FOREIGN PATENT DOCUMENTS

CA       3059665 A1   10/2018
EP       3609550 A1    2/2020
(Continued)

OTHER PUBLICATIONS

International Search Report for Application No. PCT/FR2018/000076, dated Jul. 9, 2018 (3 pages), with English Translation (2 pages).

(Continued)

*Primary Examiner* — Benjamin J Klein
(74) *Attorney, Agent, or Firm* — Schwegman Lundberg & Woessner, P.A.

(57) ABSTRACT

The present invention relates to a device and a method for FIG. 2 treating fat cells taken from a patient and intended for a transplant. More specifically, it relates to a device and a method by suctioning which makes it possible to separate the viable fat cells from the residues and elements which are not transplantable. The device is a device for treating adipose tissues (G) connected to a suctioning means (M), consisting of a sealed treatment chamber (A) comprising a means for connection (17) to said suctioning means (M), a means for inlet (13) of said adipose tissues before treatment, a filtration means (3) and at least one means for outlet (20) of said adipose tissues (G) after treatment, said filtration (Continued)

means (3) comprising a conically shaped external wall (3 1, 3) comprising a narrow base (55) attached to an impeller (25) and an internal sieving means (30) connected to the output means (20), said impeller (25) being subjected to the air pressure reduction created by the suctioning means (M) and constituting a rotary mechanical actuating means for actuating said filtration means (3).

12 Claims, 7 Drawing Sheets (52) U.S. Cl.
CPC ..... *A61M 1/785* (2021.05); *A61M 2202/0021* (2013.01); *A61M 2202/08* (2013.01); *A61M 2205/103* (2013.01); *A61M 2205/7545* (2013.01)

(58) Field of Classification Search
CPC ...... A61M 1/0281; A61M 1/88; A61M 1/892; A61M 1/895; A61M 2202/0021; A61M 2202/08; A61M 2205/103; A61M 2205/7545; C12M 45/02; C12M 45/05
See application file for complete search history.

(56) References Cited

U.S. PATENT DOCUMENTS

| | | | | |
|---|---|---|---|---|
| 7,789,872 | B2* | 9/2010 | Shippert | A61M 1/892 604/218 |
| 2008/0281256 | A1 | 11/2008 | Lee et al. | |
| 2012/0003733 | A1* | 1/2012 | Gueneron | C12M 29/06 366/331 |
| 2012/0271254 | A1 | 10/2012 | Schafer et al. | |
| 2014/0081237 | A1 | 3/2014 | Wolters et al. | |
| 2014/0193852 | A9* | 7/2014 | Vossman | C12M 45/02 435/308.1 |
| 2016/0208211 | A1* | 7/2016 | Cimino | C12M 47/04 |

FOREIGN PATENT DOCUMENTS

| | | |
|---|---|---|
| EP | 3609550 B1 | 6/2021 |
| EP | 3954403 A1 | 2/2022 |
| KR | 20190134740 A | 12/2019 |
| WO | WO 2014/039697 A1 | 3/2014 |
| WO | WO-2018189431 A1 | 10/2018 |

OTHER PUBLICATIONS

"European Application Serial No. 18727042.6, Intention to Grant dated Dec. 11, 2020", 29 pgs.

"European Application Serial No. 18727042.6, Response to Communication pursuant to Rules 161(1) and 162 EPC filed Apr. 28, 2020", 7 pgs.

"European Application Serial No. 21184172.1, Extended European Search Report dated Jan. 17, 2022", 6 pgs.

"International Application Serial No. PCT/FR2018/000076, International Preliminary Report on Patentability dated Oct. 24, 2019", 7 pgs.

"International Application Serial No. PCT/FR2018/000076, Written Opinion dated Jul. 9, 2018", 10 pgs.

* cited by examiner

DEVICE FOR TREATING FAT CELLS TAKEN FROM A PATIENT AND INTENDED FOR A TRANSPLANT

Cross reference to related applications

This application is the U.S. national phase entry under 35 U.S.C. § 371 of International Application No. PCT/FR2018/000076, filed on Apr. 6, 2018, which claims priority to French Patent Application No. 1770365, filed on Apr. 11, 2017.

FIELD OF THE INVENTION

This invention concerns a device and a method for processing fat cells taken from a patient and intended for a transplant. More specifically, it is a device and a suctioning method that allows separating viable fat cells from residues and elements that cannot be transplanted.

BRIEF DESCRIPTION OF THE PRIOR ARTS

Lipofilling or autograft of fat tissues is a technique that consists of taking small quantities of fat from a patient to reinject them into the same patient in order to fill or remodel a part of the body.

After the initial taking of the fat, it should be cleaned in order to separate the intact fat cells from other substances that are not transplantable (blood, oil coming from the explosion of poor quality cells . . . ).

To carry out this cleaning operation, different devices have been developed.

The product marketed under the Puregraft brand consists of a flexible bag including a central filtrating membrane separating two areas. The bag features a fluid inlet coming from the body of a patient and a fluid outlet for its use in another surgical intervention. The fat removed is filtered through the filtration membrane; the poor quality fat and the residues are isolated and eliminated. The use of this device is however relatively long and not very cost-effective in the end.

The product marketed under the Revolve brand by the Lifecell company allows removing, processing, and extracting the fat in a single reservoir. A system enables the loading of syringes for reinjection directly from the reservoir. The device works through a handle that must be activated by rotation after having added a rinsing solution. But this action requires human intervention and therefore ties up personnel.

Patent US/2008/0281256 describes a centrifugation device to perform liposuction then lipo-injection. The centrifuge includes an air pump for suctioning and compression. Apart from this device requiring numerous handlings, it is proven that during centrifugation, the extracted cells are subjected to very significant physical duress, which reduces their survival rate.

This invention aims to counter all these disadvantages by offering a minimally cumbersome device that allows rapid, simple, and optimal processing of the fats, while still preserving the integrity of the fat cells. The proposed device is furthermore inexpensive and very cost-effective.

SUMMARY OF THE INVENTION

This invention allows improving the technique by offering a mechanical device for the processing of adipose tissues in a patient during an adipose tissue transfer procedure.

This is an adipose tissues processing device connected to a suctioning means, comprised of a hermetic treatment chamber including a connection means to said suctioning means, an inlet means for said adipose tissues before processing, said filtration means and at least one outlet means of said adipose tissues after processing, said filtration means including a conical-shaped external wall including a narrow base attached to an impeller and an external screening means connected to the outlet means, said impeller being subjected to an air vacuum created by the aspiration means and forming a rotating mechanical actuation means of said filtration means.

Preferentially, the inlet means of said adipose tissues includes an inlet means for the cleaning fluid.

Preferably, the treatment chamber includes an outlet means for the cleaning fluid.

As per one iteration, the screening means is comprised of a screen, each of the meshes forming the screen having a dimension between 500 microns and 1 mm.

As per one variant, the filtration means includes at least one mixing means. Preferably, the treatment chamber includes a planetary gear set providing an agitation means of said adipose tissues.

As per another iteration, the treatment chamber is connected by a connection means to another electronic control of the processing method of the adipose tissues means.

Preferentially, the treatment chamber includes an attachment means.

BRIEF DESCRIPTION OF THE DRAWINGS

In this description, we refer to the appended drawings on which.

DETAILED DESCRIPTION OF THE PREFERRED ITERATIONS

As per one preferred iteration, the device is a mechanical and hermetic treatment chamber (A), that transforms an energy of a different nature into mechanical energy, and thus ensures the purification of the volume of adipose tissues by centrifugation. The operation of the processing chamber (A) is based on the transformation of an airflow or an air stream into centrifugal force.

The processing chamber (A) designates all the parts that assist or that may assist in controlling the processing method by centrifugation of the adipose tissue. This processing chamber (A) features a central area, an upper area, and a lower area. These three areas are horizontal. To facilitate the understanding of the device, the concept of the technical unit is to be defined. A technical unit is a solid mass forming a unitary body or a group of integral bodies amongst themselves. Said units are comprised of elements such as tumblers, flanges, bases, casings, holes or others, that simultaneously carry out several functions like for example "allowing a rotation" or "allowing the passage of a liquid", etc.

Figure 3:
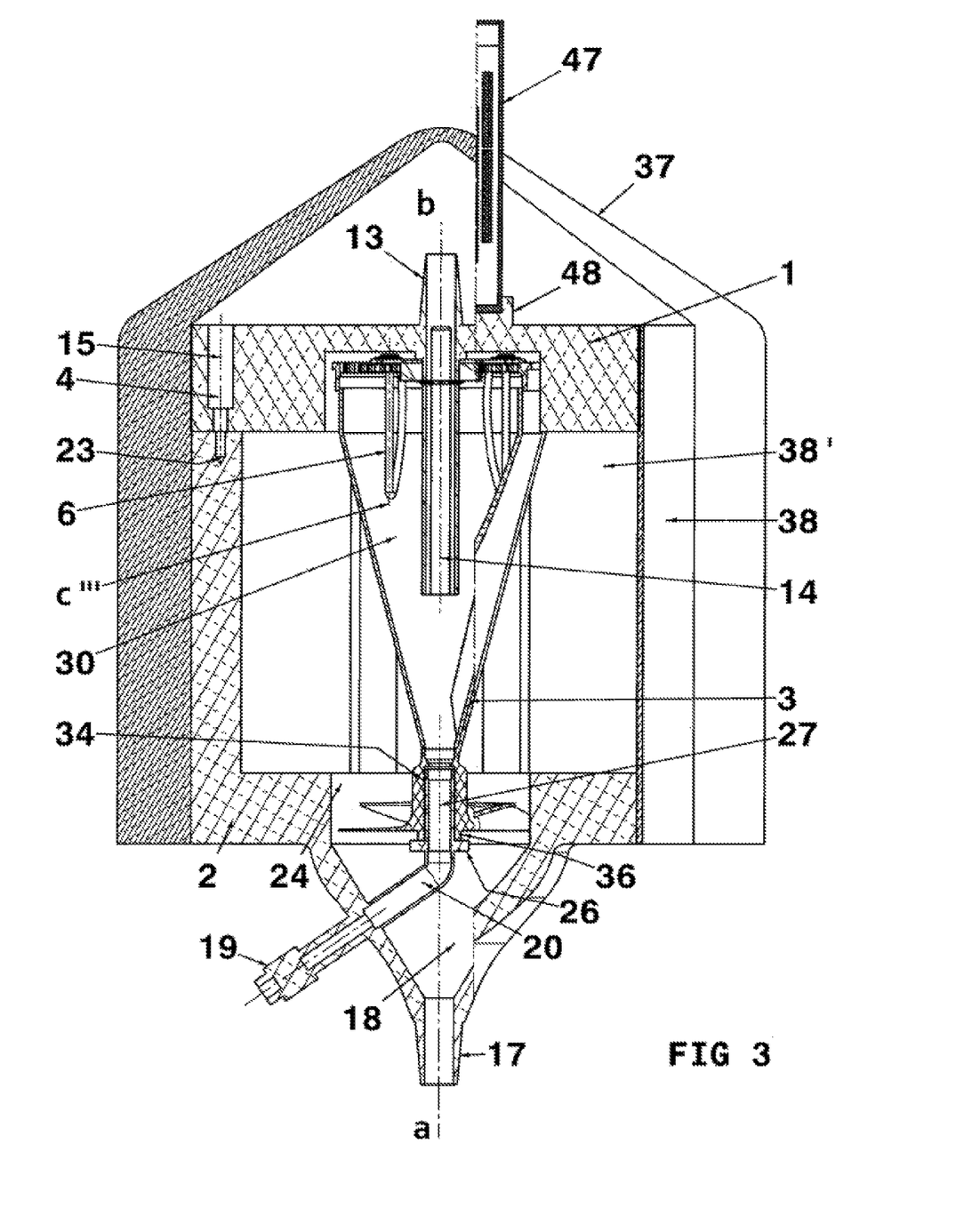
FIG. 3: Represents a sectional view of the device.
Figure 4:
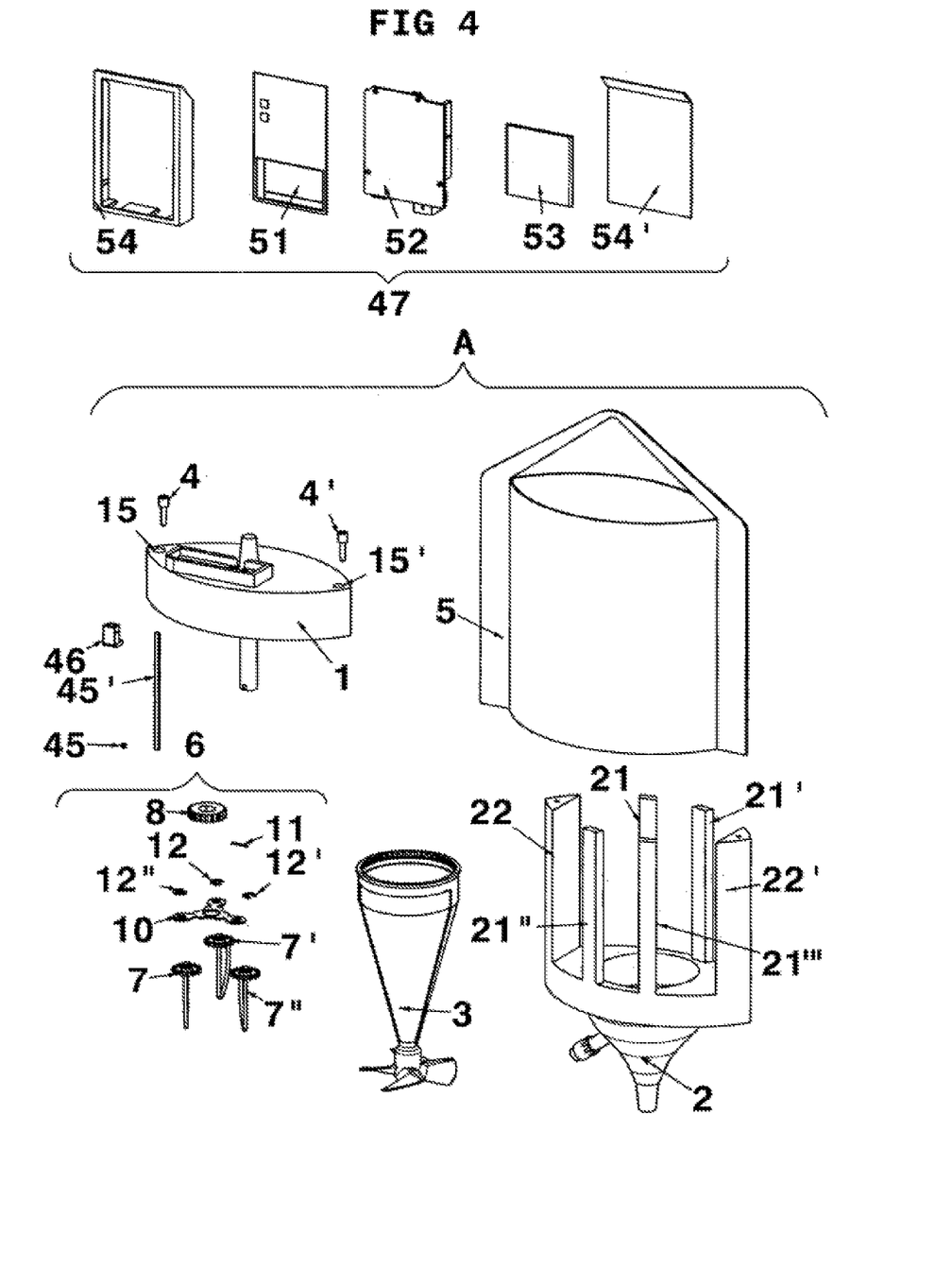
FIG. 4: Represents a side exploded view of the device.

Said processing chamber (A) is comprised of two stationary technical units called intake unit (1) and discharge unit (2), connected by two screws (4.4'). This processing chamber (A) is also comprised of a mobile technical unit called the filter (3).

Said processing chamber (A) ensures the bulk of the hermeticity through a casing (5) glued or thermally welded with the intake and discharge units (1, 2).

Said intake unit (1) located in the upper area of processing chamber (A) has the main function of supplying processing chamber (A) with air and adipose tissues adequately.

Said intake unit (1) includes a part on the outside of processing chamber (A), and a part inside processing chamber (A); each part features a central area, and an area on each side; these three last areas are noticeably vertical. Said intake unit (1) includes on its area outside processing chamber (A) an inlet means called a conical inlet orifice (13) positioned in the center, which communicates a fluid conduit (14) with the outside. The intake unit (1) also includes on its external part two holes with flat bottoms (15,15') for the introduction and fastening of two cylindrical head screws (4,4').

The intake unit (1) includes on its area on the inside of processing chamber (A), a casing (16) in which filter (3) is housed. Said intake unit (1) also includes on its area located inside the device a vertical fluid conduit (14), in a cylindrical shape. Said vertical fluid conduit (14) delivers the tissue taken (I) to be processed and a cleaning fluid (L), from the conical inlet orifice (13) to the center of the filter (3). The inlet unit (1) may include an opening with an antibacterial filter to let more air into processing chamber (A).

Figure 6:
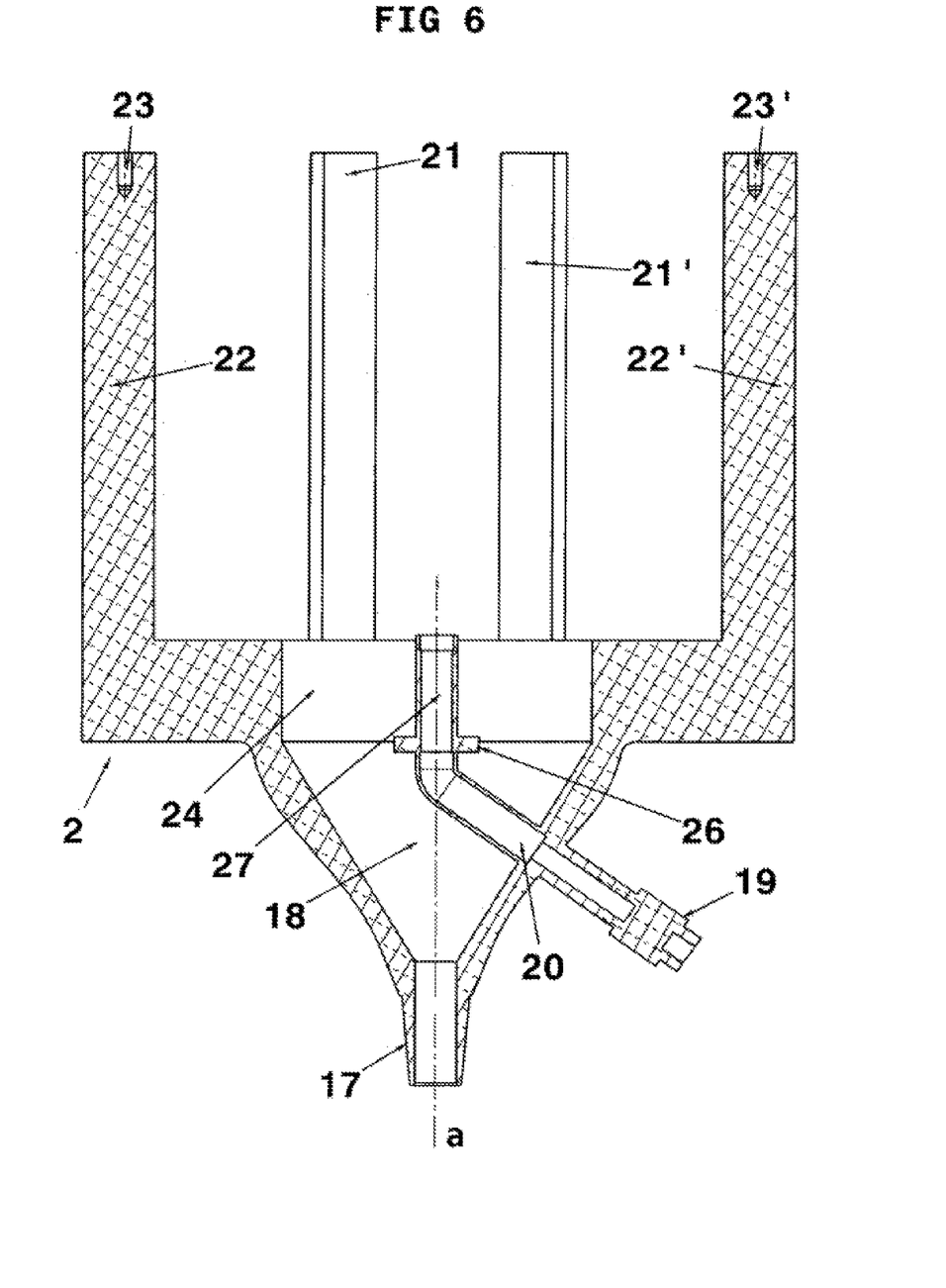
FIG. 6: Represents a sectional view of the discharge unit.

The discharge unit (2) located in the inside area of said processing chamber (A) has the primary function of discharging or evacuating the filtrate (F) and the adipose tissues (G) present in processing chamber (A).

Said discharge unit (2) includes a part outside processing chamber (A) and a part inside processing chamber (A). Each part features a central area, and an area on each size; these last three areas are noticeably vertical.

Said discharge unit (2) includes on its part outside the processing chamber a connection means called a conical output orifice (17) positioned in the center and that communicates a fluid conduit (18) with the outside. Said discharge unit (2) also includes on its exterior part a Luer Lock output orifice (19) to establish a leak-free connection between an outlet means called a fluid conduit (20) and a male syringe connect (K).

Said discharge unit (2) includes on its internal part said vertical fluid conduit (18), which discharges the air and the filtrate (F) present in processing chamber (A) towards the outside. The discharge unit (2) also includes on its internal part said fluid conduit (20) that directs the adipose tissue (G) located in the filter (3) up to the Luer Lock orifice (19). Said discharge unit (2) includes again four simple columns (21, 21', 21", 21''') in the center, which support the intake unit (1) and prevent the casing (5) from deforming under the effect of the vacuum and disturbing the proper functioning of the device, then two columns (22, 22') on the ends, connected to the intake unit (1) through threaded holes (23, 23') in the dimensions of the two screws (4, 4'). Said discharge unit (2) also includes on its internal part a casing (24) sized to allow the rotation of the filter's (3) impeller (25). Said casing (24) is equipped with a base (26) that supports the filter (3). Said casing (24) is of a cylindrical shape; it serves especially as an inlet orifice of the filtrate (F) to a fluid conduit (18). The fluid conduit (18) goes from the casing (24) up to the conical output orifice (17). The dimensions of the conduit (18) determine the general flow and thus the rotation speed of the filter (3). Said fluid conduit (20), in a cylindrical shape, is in the center of the conduit (18); it goes from an input orifice (27) at the center of the casing (24) up to the Luer Lock output orifice (19). The input orifice (27) guides the rotation of the filter (3).

Figure 7:
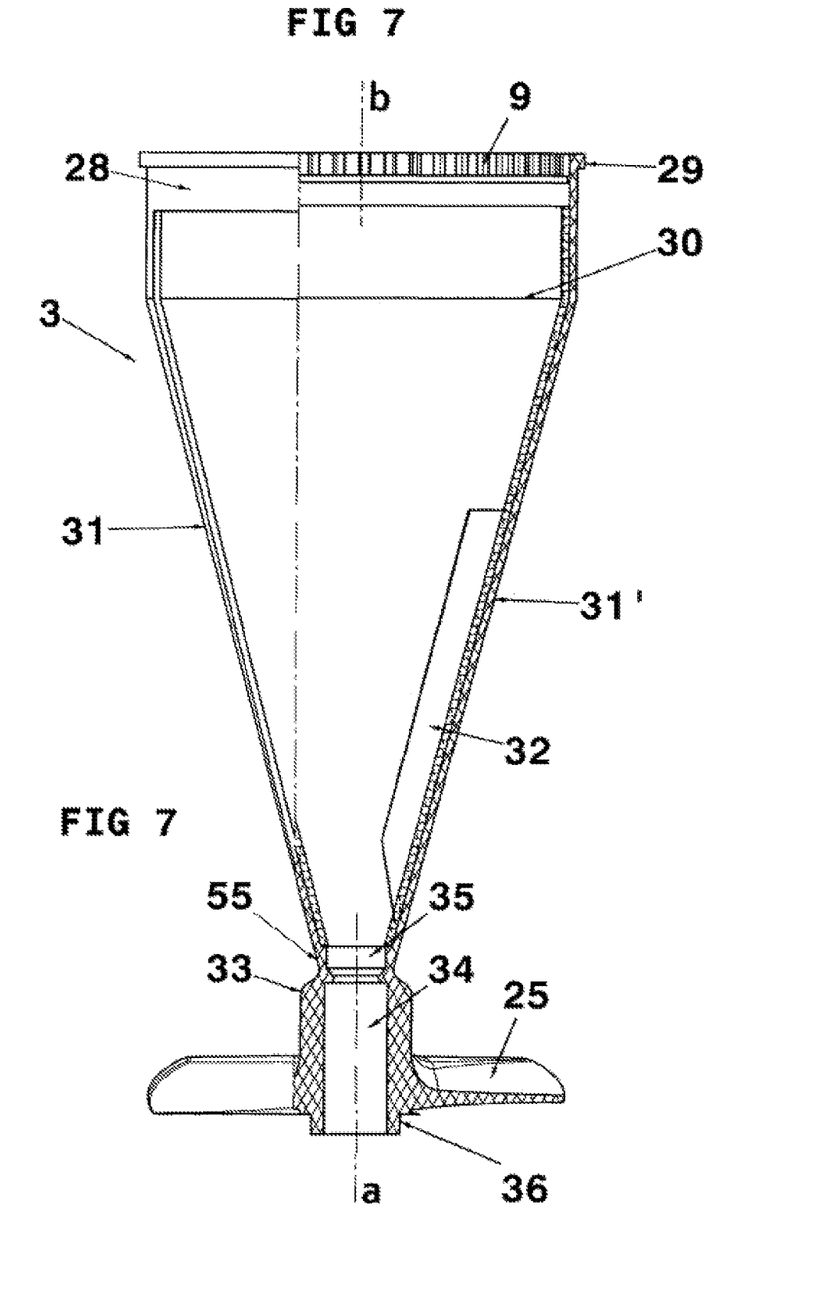
FIG. 7: Represents a sectional view of the filter.

Said filter (3) located in the central area of processing chamber (A) is a filtration means supported by the discharge unit (2), is guided in rotation by two units (1,2). Said filter (3) has the primary function is the centrifugation or the separation of components from a mixture according to the differences in density of the solid particles in suspension in a fluid, by subjecting them to a centrifugal force. Said filter (3) features a central area, an upper area, and a lower area; these three areas are horizontal.

Said filter (3) includes, on its upper area, a ring (28) and a flange (29), intended to receive elements from rotation speed measurements.

Said filter (3) includes on its central area a screen (30) that traps the tissue (G) and discharges the filtrate (F). The confined volume of the adipose tissues (G) inside the screen (3) is alternatively called a retentate (G). The conical shape of the internal screening means (3) allows directing the adipose tissue (G) internally and obtaining at least 80% to 95% of the available processing volume. The screen (30) may be sized with a mesh within a range of 500 microns to 1 mm. The screen (30) may be of any design, any porous structure. The screen (30) may be glued, welded, or molded to the filter (3) from a narrowed base (55) to a ring (28). The available retentate (G) in the screen may be within a range having a lower limit of 50 cubic centimeters, and an upper limit of 350 cubic centimeters. Said screen (30) is made rigid by two conical supports (31,31') that also support the ring (28) and form the wall of the filter (3). Said filter (3) also includes two mixing means called mixers (32), that have the purpose of agitating the fats (G), during the rotation of the filter (3). The two mixers (32) are placed on two supports (31,31'). The two mixers (32) allow improving the cleaning and the transfer of the organic materials towards the screen (30).

The filter (3) includes on its lower area a rotating mechanical actuation means of said filtration means, a four-blade impeller (25) that transforms the energy of the suctioning flow into mechanical energy. The rotation of the impeller (25) around its axis is guided by the input orifice (27) of the discharge unit (2). The number of blades may vary in order to optimize the impeller's (25) yield. The impeller (25) is comprised of a minimum of two blades joined by the central part called a hub (33). The impeller's (25) torque is related to the airflow. The end of the blades has a more significant linear speed than the blade sections in the center. The mechanical energy produced by the impeller (25) depends on three parameters: the shape and the length of the blades, the speed of the filtrate, then finally the temperature, which influences the density of the filtrate (GF). The power of the impeller (25) depends primarily on the energy of the filtrate (F) and its variations. The mechanical energy of the impeller (25) is therefore an intermittent energy. In practice, the impeller (25) produces four times more energy if the blades are two times larger and eight times more energy if the suctioning flow doubles. The density of the filtrate (F) also comes into play; the impeller (25) produces 3% more power if, for the same speed, the filtrate (F) is colder than 10° C. The maximum power that may be recovered from the impeller is given by Betz's law, which is equal to the product of the multiplication of the atmospheric pressure with the swept surface and the cube of the speed of the filtrate (F). As a consequence, the atmospheric pressure, the swept surface, and the speed of the filtrate (F) are proportional amongst themselves and vary if one of them varies. The filter (3) includes in the center of the hub (33) a fluid conduit (34) that collects through its input orifice (35) the healthy tissue (G) in the screen (30) and the conduit to the orifice of the discharge unit (2). The filter includes a flange (36), that has the purpose of reducing the surface in contact with the base (26), and thus reducing the friction during the rotation of the filter (3). The filter (3) rests on the base (26) of said discharge unit (2). The filter (3) may include some weights, which are masse, in order to modify its balance or its inertia, in order to increase the speed.

The casing (5) that surrounds all the technical units (1,2,3) forms the walls (38,38') of the processing chamber. Said casing (5) ensures the essential functions of the hermeticity of processing chamber (A). Said casing (5) features a lower area (internal or lower) and an upper area; these two areas are horizontal.

Said casing (5) includes on its upper area an attachment means called a loop (37) which is used to retain or to carry processing chamber (A).

Said casing (5) includes on its lower area two walls (38,38') glued or thermally welded with the units (1,2). This casing (5) may be made of flexible plastic, for example, the same ones that can be found on physiological fluid bags. The casing (5) protects the adipose tissue (G) from external elements and more specifically light rays, dust, and micro-organisms or infectious agents.

The casing (5) may be made of a material configured for low, mid, and high suction. Said casing (5) may also be anti-ultraviolent (UVA, UVB) and blue light treated. The UV treatment is an essential criteria both for protecting the adipose tissue (G) from the dangers of the sun and also to ensure guarantee safety for the adipose tissue (G) from temperature variations.

Figure 5:
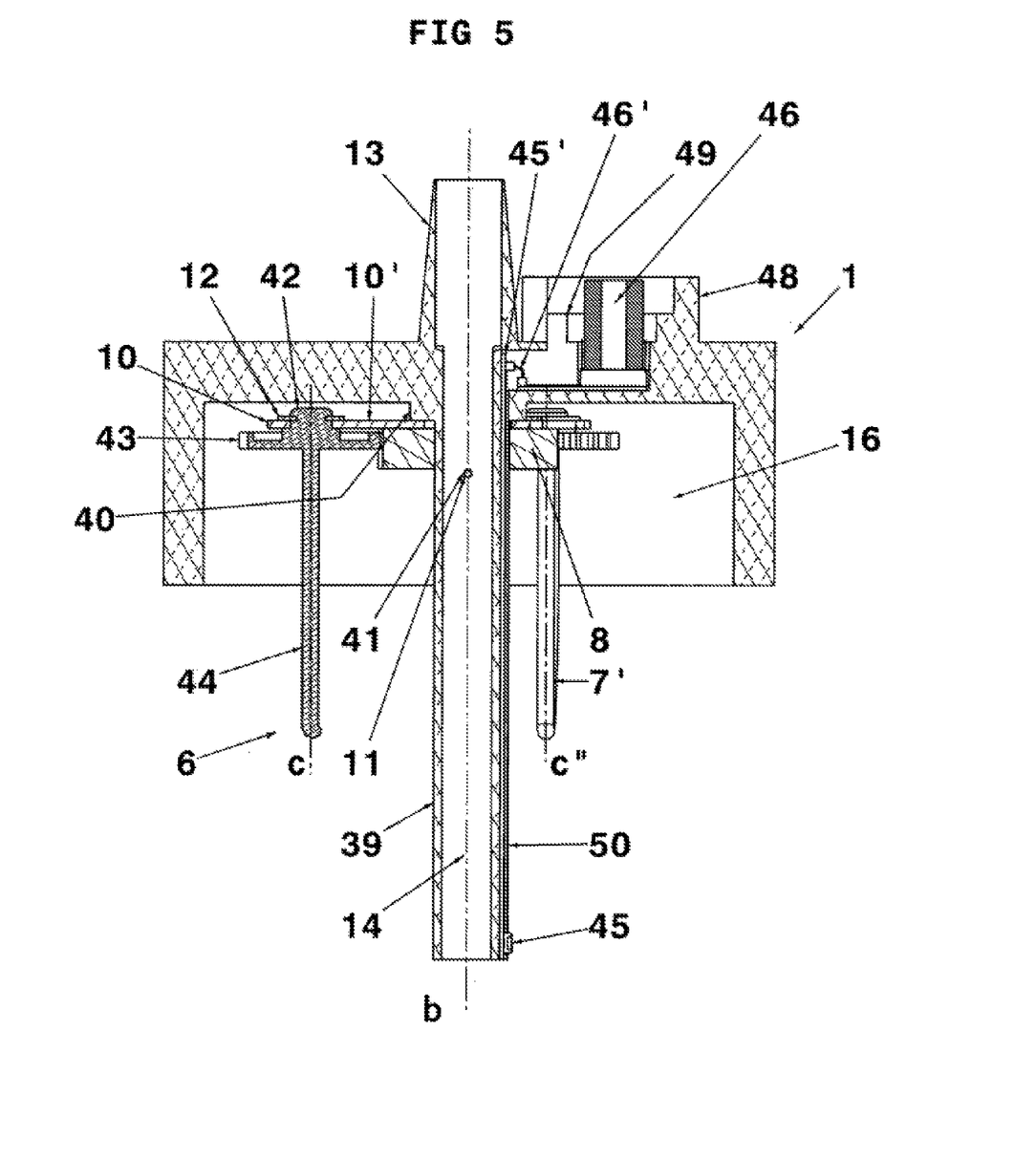
FIG. 5: Represents a sectional view of the intake unit with a planetary gear set.

As per one iteration, when processing chamber (A) includes a large processing volume, the chamber features a mechanism that agitates the volume of the adipose tissue (G) by moving it from the bottom towards the top, and around the axis (a) of the rotation of the filter (3). This agitation means of said adipose tissues is otherwise known as a planetary gear set (6). A gear set is deemed planetary when it has the special characteristic of having two degrees of mobility. During operation, the cogwheels or sprockets that make up the set do not turn around fixed axes, which gives them a planetary path, from which the name given to the set (6). Said planetary gear set (6), located in the upper area of the processing chamber (A), is housed in the casing (16) of said intake unit (1). Composed of gears, this planetary gear set (6) features an internal planetary area, an external planetary area, and a satellite area between the two previous areas. These three areas are coaxial. Said planetary set (6) includes two coaxial shafts called planetaries (8,9) and three satellites (7, 7',J") engaging with the two planetaries (8,9). Said internal planetary (8) is sometimes called a sun, and the external planetary (9) called a crown. In this version, said planetary gear set (6) of said processing chamber (A) is comprised also of a satellite door (10) and a pin (11). In addition, the ring (28) of the rotating filter (3) integrates a crown with internal gear teeth (9), and the conduit of the intake unit (1) integrates a flat bar (39), a flange (40), and a drilled hole (41). The mechanism is housed in the casing (16) of the intake unit (1), between said flange (40) of the intake unit (1) and said pin (11) housed between the drilled hole (41) of the fluid conduit (14).

Said crown (9) of the filter (3) located in the external planetary set of said set (6) of processing chamber (A) distributes the power to the various agitators (7,7',7') in a balanced way.

Said planetary agitators (7,7', 7") located in the satellite area of said set (6) of processing chamber (A) each feature a central area, an upper area, and a lower area. These three areas are horizontal. These three planetary agitators (7,7', 7") are of equivalent dimensions and appearance, but may feature different configurations. The planetary agitators (7, 7', 7") mix the adipose tissue (G) primarily with two movements; from the periphery to the center and vice versa, and/or from the bottom towards the top.

Said agitators (7, 7', 7") are each comprised on their upper areas of a shaft in a pivoting link with the satellite door (10). Each shaft receives an elastic ring (12, 12',12"). Said elastic rings, otherwise known as circlips (12, 12', 12"), are intended to maintain the shafts (42) in position.

Said agitators (7, 7', 7") are composed on their central areas of three sprockets (43) with right gear teeth. The trajectories of the points of the sprockets (32) in relation to the intake unit (1) are planetary curves, from which the name of the device comes. The gear teeth of sprockets (43) are in contact with the gear teeth of the two planetaries (8,9). Said agitators (7, 7', 7") agitate the tissue (G) at a speed lower than the speed of the mixers (32) of filter (3). Said agitators (7, 7', 7") are each comprised in their lower areas of a beater (44) to mix or agitate the retentate (G) composed of the tissue taken (I), physiological liquid (L), and air. During the operation of the device, said beaters (44) agitate the tissue (G) following a trajectory around axis (b) and a trajectory around axes (c,c'c"). Said planetary agitators (7, 7', 7") turn around their axes (c,c',c") in movement in relation to the axis (b) of the conduit (14). Said agitators (7, 7', 7") turn around a fixed wheel (8), affixed to the intake unit (1), of a large size, ensuring a silent and precise rotation, even under difficult working conditions. Said fixed wheel (8) supports the satellite door (10). The rotation of the fixed wheel (8) is stopped by the flat bar (39); its vertical position is determined by the pin (11) in the drilled hole (41).

Said agitators (7,7',7") are comprised on their lower areas of three beaters (44). Said beaters (44) are in contact with the adipose tissue (F). Said beaters (44) have the function of agitating and separating the components of the retentate (G). The shape of the beater (44) may be modified to allow better processing of the fats (G).

Said satellite door (10) is housed between the flange (40) of intake unit (1) and the affixed wheel (8). Said satellite door (10) functions as a crank turning around axis (b) and conduit (14). Said satellite door (10) features three equidistant 120-degree cranks (1). Each crank (10) includes a holding where agitators (7, 7', 7") are housed. Said cranks (10) transform into rotation movement around axis (b) one or several forces transmitted by agitators (7, 7', 7").

Said pin (11) and its drilled hole (41) have the goal of defining the horizontal positions of the fixed wheel (8) and the satellite door (10), and consequently, the positions of the agitators (7, 7', 7"), while still guaranteeing the proper functioning of the planetary set (6). Said pin (11) and its drilled hole (41) allow a compromise between the precision required for the satisfactory operation of said planetary set (6) and the technical and economical constraints of manufacturing.

Said conduit (14) of the intake unit (1) integrates a flat bar (39). Said flat bar (39), also called a flat, is a flat surface on a fluid conduit (14) of a cylindrical shape. This flat bar (39) impedes the movement of the fixed wheel (8), in order to block its rotation voluntarily.

An overly humid or overly dry volume of adipose tissue (G) may lead to asphyxia, lethal ischemia of the adipocyte fat cells (G), which may lead to poor results, unpleasantness, or even health risks. Hence controlling the process during processing may prove vital for the adipocyte fat cells (G).

As per another variant, said processing chamber (A) then features a set of material, software, and modifications in processing chamber (A) used to monitor or control the processing method of the adipose tissue (G). As per this preferred iteration, said processing chamber (A) may feature the integration of electronic components (45,45',46,46'), as well as a certain number of modifications of the intake unit (1) related to these electronic components. As per this preferred iteration, said processing chamber (A) may also feature a monitor (47) displaying humidity rates and temperatures collected by the electronic components (45,45',46, 46') of said processing chamber (A), so that the user may control the condition of the cells (G).

As per this preferred iteration, said process control is ensured in processing chamber (A) by at least one active electronic component called a sensor (45), which allows the measurements of humidity and temperature. To facilitate the description, a single sensor is represented. However, the processing chamber (A) may be equipped with speed, temperature, humidity, and luminosity detectors, jointly or independently. Said sensor (45) collects the humidity and temperature values of the adipocytes (G) without altering their qualities and transmits them through its electronic circuit (45'). Said electronic circuit (45') transmits the data revealed by said sensor (45) to the connection means called a USB port (46) through the connector (46').

As per this preferred iteration, the intake unit (1) includes on its exterior part a base (48) for electronic control means called a monitor (47), as well as a housing for the male USB port (46) 2.0 or 3.0. In said version, the intake unit (1) features on its internal part a fluid conduit (14) with reduced dimensions to leave room for an electronic conduit (50). Said electronic conduit (50) runs along the fluid conduit (14) of the housing (49) up to the center of the filter (3). Said electronic conduit (50) also allows avoiding any risk of short circuit. Said beaters (44) may also be offered in a range as needed; they may both include a temperature sensor, a humidity sensor, a luminosity sensor, or remain simple.

As per this preferred iteration, said monitor (47) allows the device's communication with the user. Said monitor (47) is composed of a TCT or LCD screen (51) that displays the result of a measurement. The display may be analog, i.e., with the unique characteristic of having a system of indicators of temperatures or humidity that is done through the displacement of a needle on a gauge, or digital, i.e. with the indications directly in the form of numbers or letters. Backlighting may be integrated into the screen (51).

The monitor (47) integrates a programmable micro or nano card (52) that has an easily programmable microcontroller, as well as numerous inputs and outputs. It is useful to point out that several microcontrollers exist; they are differentiated by the power of the microcontroller or by the size and the consumption of the card. The selection of the type of card is done based on needs. The card (52) is programmed using free programming software.

The monitor (47) integrates a lithium-ion battery (53), with a rigid shell or sheathed. Said lithium-ion battery allows significant autonomy with a limited volume and weight. Said battery (53) has a protection circuit and does not require any external protection against overload, polarity inversion, or possible charger defect. In addition, the monitor (47) may be directed powered by a charger of which the tension is between 7 and 12 volts.

The monitor integrates a casing solution with a shell (54) and a cover (54'). The shapes of said shell (54) and cover (54') may be modified if needed. Said shell (54) and cover (54') provide protection against humidity or simply against impacts.

It is important to point out that in this version of the device, the electronic components (45, 45',46) in the processing chamber (A) depend on the monitor (47) in terms of energy. The monitor (47) may communicate with the processing chamber (A) by wired connection (USB, jack, fiber optics, etc.). However, other designs may allow the processing chamber (A) to be energy independent. As per one variant, processing chamber (A) has a dynamoelectric function linked to the rotation of the filter (3), or as per another variant, processing chamber (A) has a motor and a battery, etc. So, processing chamber (A) may send the graphic values to a computer, a printer, a smartphone, or a touch screen tablet, through wireless transmission (Bluetooth, Wifi, text, email, etc.).

It should be added that a certain number of improvements, individual supplementary functions, or a combination are applicable to the invention.

Each of the elements may, but not mandatorily, be used with any other characteristic or combination. The device may be composed of any approved construction material; each part, component, or ensemble may be composed of one or several plastic compositions. The device may be configured with a very practical size for an optimal use of the collection volume. The device is designed for transportation (moved to other various places where a variety of processing of the collected tissue may be done). The device may be packaged in a sterile and hermetic environment, in packaging for transportation or storage in a tissue bank before use. The device may be sterilized in advance by dry heat, by steam from saturated water, or after packaging by exposure to plasma. To prevent risks associated with misuse, it may be cut with scissors, in order to damage the device in a way that makes it unsatisfactory for reuse.

The device may be portable and easily transportable between the places where various collection and treatment operations may be conducted.

Figure 1:
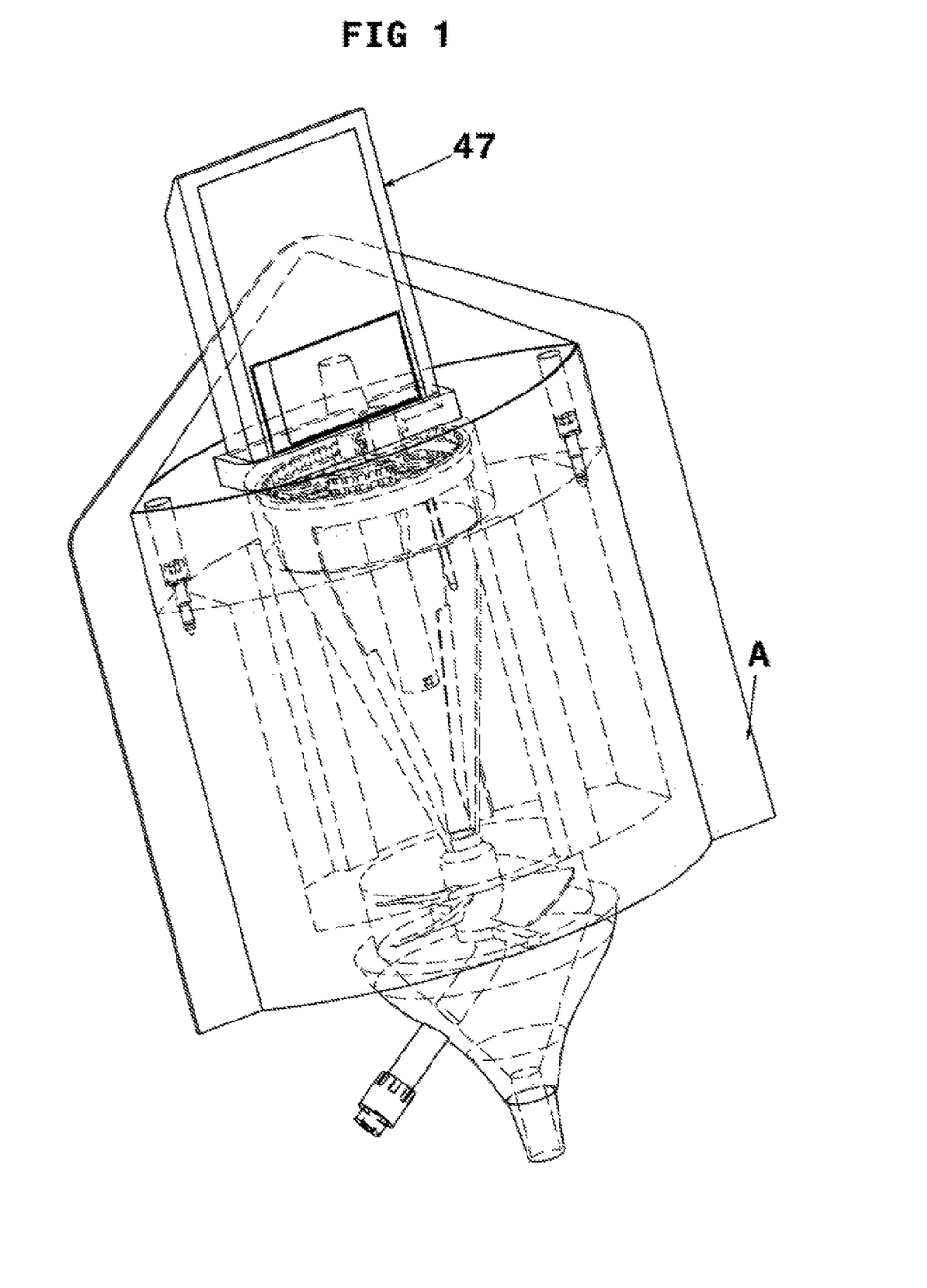
FIG. 1: Represents a side view of the device.
Figure 2:
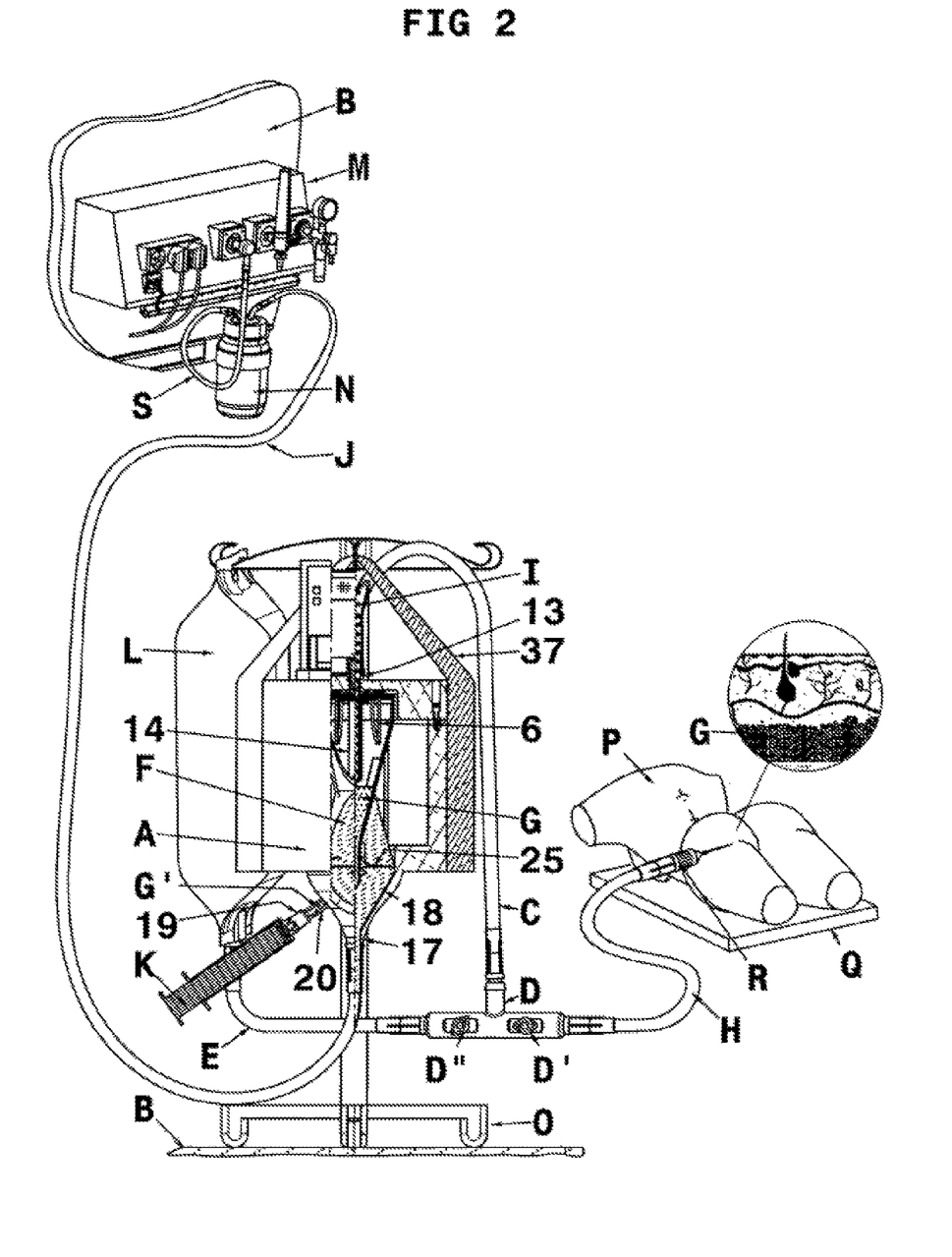
FIG. 2: Represents a view of the implementation and preparation of the device before operation.

To use the device, the user needs:

an operating theater or room (B)

a patient (P) represented in the figures by a mannequin on an operating table (Q).

a suctioning means or system (M) with a collection system (N).

an IV stand, called a drip stand (O).

a bag of physiological fluid (L).

a cannula (R) to allow suctioning without damaging the tissues.

A three-way valve (D) in the shape of a T".

Four surgical tubes (C, J, E, H, S) with a conical connector.

A syringe (K) with a Luer lock connector.

Said operating theater or room (B) is designed so as to optimize the patient's safety and to contribute to infection prevention steps. Operating rooms have as a general rule latest generation equipment. These rooms have high performance and modular medical devices, adapted to perform complex surgical procedures but also to facilitate university teaching The patient (P) is prepared for outpatient surgery, or more simply, a surgery scheduled and performed in the technical conditions mandatorily requiring the safety of an operating room, under variable mode anesthesia, followed by postoperative surgery allowing, without increased risks, the patient's discharge the same day of his/her intervention. Said surgical procedure is identical to the one performed in classical surgery with complete hospitalization. There does not exist any specificity either for the anesthesia. It is not the procedure that is outpatient, but the patient.

The operation of processing chamber (A) is based on the airflow and on the centrifugal force. Hence, the processing chamber (A) works with any type of suctioning means. However, ideally, and for ease of understanding, said suctioning means is a technical platform (M) allowing connection to the medical fluid sockets, to the electrical sockets, and to the Ethernet ports of the equipment in the operating and intensive care rooms. Said technical platform (M) is integrated into the operating room (B). The technical platforms may be configured depending on needs. Therefore, any additional accessory may be added to the technical platform (M) such as electrical sockets, gas sockets, nurse call buttons, light switches, etc. Said technical platform (M) is connected fluidly to the collection (N) by a hose (S).

Said IV stand (O) otherwise known as a drip stand is a mobile element where a bag or a perfusion flask is hung in order to allow the patient to move. Said IV stand (O) is either on wheel for greater mobility or fixed to the bed for minimum encumbrance.

The physiological fluid (L) is generally comprised of distilled water and sodium chloride and presents no danger to the body. It is currently used for medical purposes in particular for vascular filling in intravenous perfusion, the cleaning of wounds, or the temporary preservation of organs separated from the body in a condition conducive to observation, analysis, or graft. The physiological fluid (L) is improperly called physiological serum but does not come directly from the blood.

The processing chamber (A) operates with different sampling methods in a patient, or with tissues packaged by a tissue bank. Hence, a small tube or hose allowing the passage of tissues and fluid through an orifice obtained after surgical intervention on the patient (P) or suffices for the proper functioning of the processing chamber (A). However, and for ease of understanding, the use of a sampling cannula (R) is used in the transfer procedures of the tissues taken (I), during the stage of taking adipose tissues (G) within the patient's body (P). Said cannula (R) does not feature any protruding corners or edges and does not leave any pressure points.

Said 3-way valve (D) has two injection sites, each with an operating lever (D',D"). The first operating lever (D') controls the flow of the suctioned sample, and the second lever (D") controls the flow of physiological fluid. Said valve (D) may be automated through a servomotor or ensuring the conversion of a movement control signal of the operating levers (D', D"). As per another iteration in which the sampling of tissues (I) and the physiological fluid (L) are mixed only in the processing chamber (A), said 3-way valve (D) is replaced either by two orifices (13) for the fluid conduit (14) of the intake unit (1) or by a second fluid conduit identical to the fluid conduit (14).

Said surgical tubes (C,J,E,H,S) maintain their shapes perfectly during suctioning. Each end is equipped with universal female connectors for practical and secure fixation. Two tubes (C,J) are used respectively to connect fluidly the processing chamber (A) to the valve (D) output and the collection (N) of the technical platform (M), as well as two tubes (E,H) which are used respectively to connect fluidly the inputs of the valve (D) with the physiological liquid (L) and the suctioning cannula (R).

For preparation, the following stages must be respected: installing processing chamber (A) by its loop (37) on the drip stand (O). Installing the physiological serum (L) on the drip stand (O). Connecting a first tube (C) to the input orifice (13). Connecting tube (J) of the collection (N) to the processing chamber (A)'s filtrate output orifice (17). Connecting the Luer lock syringe (K) to the Luer lock output (19) of processing chamber (A). Checking that levers (D') and (D") of the valve (D) are closed. Connecting tube (C) to the output orifice of valve (D). Connecting the physiological serum (L) onto the first input orifice of valve (D) using a tube (E). Connecting hose (H) of the suctioning cannula onto a second input orifice of valve (D). Installing the monitor (47) on the base (48). Turning on the monitor (47). Activating the suctioning.

Processing chamber (A) may include a mechanical on/off function of the centrifugation of the filter (3) located on the outside.

The total opening of lever (D') of valve (D) allows the user to sweep with the cannula (R) the area where the tissue (I) must be taken and allows activating the processing chamber (A) mechanically. Through the effect of suctioning flow, the impeller (25) activates and transforms the energy of the suctioning flow into mechanical energy, into rotation movement. The centrifugation phase then begins.

The partial opening of lever (D") of valve (D) allows the physiological fluid (L) to move along the tube (E), under the effect of gravity and the vacuum, up to the valve (D). The partial opening of lever (D") also allows controlling the flow of the physiological fluid (L). The tissue sampled (I) and the physiological fluid (L) are mixed in the valve (D) to come out again in the tube (C). Tube (C) moves the "physiological fluid (L)/sampled tissue (I)" mixture towards the orifice (13) of the processing chamber (A). The "physiological fluid (L)/sampled tissue (I)" mixture crosses the conduit (14) and is then deposited in the screen (30) of the filter (3). The filter (3), using mixers (32), agitates the "physiological fluid (L)/sampled tissue (I)" mixture and only retains the fats or the adipose tissues. In addition, the physiological serum (L), both hydrophilic and hydrophobic, binds onto the organic materials that water alone cannot remove by discharging them through the screen (30) as the result of inertia. The screen (30) confines a retentate (G), and releases the cleaning fluids and matter of smaller sizes. When the processing chamber includes a planetary set (6), the agitators (7,7',7") agitate the adipose tissue (G) inside the filter (3), which improves its processing and its rinsing. The mixture discharged through the meshes of the screen (30) is called a filtrate (F). Filtrate (F) is brought outside the screen (3), towards the fluid conduit (18) of said discharge unit (2), then discharged by the output orifice (17) into pipe (J) up to the collection (N) of technical platform (M).

As a result of gravity, filtrate (F) falls into conduit (18). Filtrate (F) is then discharged continuously. In its path, filtrate (F) wholly conveys work to the impeller (25), which reduces the torque, increases the nominal speed of the rotation of the filter (3). Filtrate (F) is moved along conduit (18) as a result of the gravity and the vacuum.

A small volume of adipose tissues (G) is moved along the conduit (20); this volume is not processed or is barely processed' it must therefore be removed then thrown away.

One the required volume of tissue (G) has been reached, leave levers (D') and (D") of valve (D) open until the filtrate (F) is comprised mainly of physiological serum (L). The intake unit (1) may include an opening with an antibacterial filter to increase the flow in processing chamber (A) and the speed of the filter (3). When the filtrate (F) is comprised mainly of physiological serum (L), close the lever (D″). In said version in which the device includes a monitor (47), control the rate of humidity and temperature observed by the sensor (45) on the monitor (47). All throughout the processing operation of the adipose tissue (G), the user may control the condition of the adipose tissue (G) on the monitor (47).

When the condition is satisfactory, closer lever (D′) of valve (D). Stop the suctioning system. Suction the volume of unprocessed tissues (G′) lodged in the conduit (20) using the syringe (k). Empty the contents of the syringe in an appropriate container. Insert the syringe (k) into the Luer lock port and extract the retentate (G) contained in processing chamber (A) in order to graft it. The conical shape of the filter (3) allows directing the tissue (G) within it, and to get 80% to 95% of the available processed volume. The use of a processing chamber (A) is a donor for several recipients. Hence the user may take several tissue samples from one donor and regraft them onto different recipients.

After use, the device may be placed in the trash or into waste sorting appropriately.

Numerous variants that can possibly be combined may be brought here while remaining within the framework of the invention as it is defined above.

Insubstantial modifications that would derive obviously for man from the art, the use, or the manufacture for which the patent is here required without changing its original provisions would only be simple technical equivalents and fall within the framework of this invention.

INDUSTRIAL APPLICATIONS

The device may be used for various processing applications involving adipose tissues.

The device may be used for various applications like lipofilling, mammary construction—reconstruction, scar filling, etc.

The device may be used for the pre-analysis processing of adipose tissue and may allow the performance of several different operations when it is in operation.

The device may be used for the preparation of concentrates, or in order to separate the parts of the tissue taken.

The invention claimed is:

1. A device for processing adipose tissue, the device comprising:
    a mechanical and hermetic treatment chamber comprising:
        two stationary units including an intake unit supported by a discharge unit, the intake unit including an inlet in communication with a first fluid conduit;
        a filter disposed in a central area of the chamber, wherein the filter comprises a screen and an impeller configured to provide centrifugal force to separate a filtrate from the adipose tissue,
            wherein the first fluid conduit is configured to deliver the adipose tissue from the inlet to the filter;
            wherein rotation of the impeller transforms a suctioning flow into the centrifugal force; and
            wherein the discharge unit includes a second fluid conduit to discharge the filtrate and a third fluid conduit to discharge the tissue; and
        a casing around the intake unit, the discharge unit, and the filter.

2. The device of claim 1, wherein the screen is a mesh screen.

3. The device of claim 2, wherein the mesh screen has a mesh opening size of between 500 microns and 1 mm.

4. The device of claim 2, wherein the screen and the filter have a conical shape to direct the adipose tissue within the filter.

5. The device of claim 1, wherein the suctioning flow applied to the mechanical and hermetic treatment chamber is from an external suctioning platform.

6. The device of claim 1, wherein the discharge unit comprises four columns that support the intake unit.

7. The device of claim 1, wherein the filter rests on a base of the discharge unit.

8. The device of claim 1, wherein the mechanical and hermetic treatment chamber further comprises a sensor adapted to measure humidity and temperature within the mechanical and hermetic treatment chamber.

9. The device of claim 8, wherein the device further comprises a monitor to display a measurement, wherein the measurement is collected by the sensor and the sensor is communicatively linked to the monitor.

10. The device of claim 9, wherein the monitor communicates with the mechanical and hermetic treatment chamber by wired connection or wireless connection.

11. The device of claim 9, wherein the monitor comprises a programmable micro or nano card with a programmable microcontroller.

12. The device of claim 1, wherein the mechanical and hermetic treatment chamber comprises a motor and a battery.

* * * * *

UNITED STATES PATENT AND TRADEMARK OFFICE
CERTIFICATE OF CORRECTION

| | | |
|---|---|---|
| PATENT NO. | : 11,602,587 B2 | |
| APPLICATION NO. | : 16/604307 | |
| DATED | : March 14, 2023 | |
| INVENTOR(S) | : Najib Taizou | |

It is certified that error appears in the above-identified patent and that said Letters Patent is hereby corrected as shown below:

On the Title Page

Item (73), in "Assignee", in Column 1, Line 1, delete "Establishment Labs S A," and insert --Establishment Labs S.A.,-- therefor Signed and Sealed this
Eleventh Day of June, 2024

Katherine Kelly Vidal
*Director of the United States Patent and Trademark Office*